(12) United States Patent
Montgomery et al.

(10) Patent No.: US 6,949,640 B2
(45) Date of Patent: Sep. 27, 2005

(54) METHOD FOR SYNTHESIZING 2-CHLORO-9-(2-FLUORO-β-D-ARABINOFURANOSYL)-9H-PURIN-6-AMINE

(75) Inventors: John A. Montgomery, Birmingham, AL (US); Anita T. Fowler, Birmingham, AL (US); John A. Secrist, III, Birmingham, AL (US)

(73) Assignee: Southern Research Institute, Birmingham, AL (US)

(*) Notice: Subject to any disclaimer, the term of this patent is extended or adjusted under 35 U.S.C. 154(b) by 323 days.

(21) Appl. No.: 09/889,287

(22) PCT Filed: Feb. 16, 2001

(86) PCT No.: PCT/US01/05320

§ 371 (c)(1),
(2), (4) Date: Jul. 16, 2001

(87) PCT Pub. No.: WO01/60383

PCT Pub. Date: Aug. 23, 2001

(65) Prior Publication Data

US 2003/0023078 A1 Jan. 30, 2003

Related U.S. Application Data

(60) Provisional application No. 60/183,422, filed on Feb. 18, 2000.

(51) Int. Cl.[7] .............................................. C07H 19/19
(52) U.S. Cl. .................. 536/27.4; 536/26.71; 536/124; 536/26.8; 536/27.63; 536/22.1; 536/27.1; 536/27.13; 536/27.21; 536/27.6; 536/27.61; 536/28.1; 536/55.3; 514/43; 514/45; 544/277; 544/265; 548/253
(58) Field of Search ............................ 536/27.4, 26.71, 536/124, 26.8, 27.63, 22.1, 27.1, 27.13, 27.21, 27.6, 27.61, 28.1, 55.3; 514/43, 45; 544/277, 265; 548/253

(56) References Cited

U.S. PATENT DOCUMENTS

| | | | | |
|---|---|---|---|---|
| 4,625,020 A | * | 11/1986 | Brundidge et al. | ........ 536/18.2 |
| 4,751,221 A | * | 6/1988 | Watanabe et al. | ............. 514/46 |
| 4,918,179 A | * | 4/1990 | Watanabe et al. | ............. 536/24 |
| 5,180,824 A | * | 1/1993 | Bauman et al. | ............. 544/251 |
| 5,310,732 A | * | 5/1994 | Carson et al. | ................. 514/46 |
| 5,384,310 A | | 1/1995 | Montgomery et al. | |
| 5,401,838 A | | 3/1995 | Chou | |
| 5,821,357 A | * | 10/1998 | Chou et al. | ................. 536/55.3 |

FOREIGN PATENT DOCUMENTS

| | | |
|---|---|---|
| EP | 0 314 011 A2 | 5/1989 |
| EP | 0 577 303 A1 | 1/1994 |
| WO | WO-89/08658 A1 | 9/1989 |
| WO | WO-92/09604 A1 | 6/1992 |
| WO | WO-92/20347 A1 | 11/1992 |

OTHER PUBLICATIONS

"Studies on the Axidoazomethine–Tetrazole Equilibrium. V. 2– and 6–Azidopurines" Temple, Jr. et al., Temple, Kussner, and Montgomery, vol. 31 pp. 2210–2215, Feb. 28, 1966.

(Continued)

Primary Examiner—James O. Wilson
Assistant Examiner—Devesh Khare
(74) Attorney, Agent, or Firm—Connolly, Bove, Lodge & Hutz, LLP

(57) ABSTRACT

2-Chloro-9-(2-deoxy-2-fluoro-β-D-arabinofuranosyl)-9H-purin-9-amine is synthesized by reacting a 2-chloro-6-substituted purine with a protected and activated 2-deoxy-2-fluoro-D-arabinofuranose; and reacting with a base such as ammonia to provide 2-chloro-9-(2-deoxy-2-fluoro-β-D-arabinofuranosyl)-9H-purin-6-amine. When the purine reactant is substituted in the 6 position with a halogen, a reaction step with an alkoxide is carried out prior to the reaction with ammonia.

34 Claims, 3 Drawing Sheets

OTHER PUBLICATIONS

"Correlation of the Proton Magnetic Resonance Chemical Shifts of Substituted Purines with Reactivity Parameters. 1. 2,6–Disubstituted Purines", Coburn Jr., et al. Coburn, Thorpe, Montgomery, and Hewson. vol. 30, pp. 1110–1113. Nov. 16, 1964.

"Synthesis of 6–Aryloxy– and 6–Arylalkoxy–2–chloropurines and Their Interactions with Purine Nucleoside Phosphorylase from *Escherichia coli*.", Bzowska et al., J. Biosci. 1999, vol. 54, pp. 1055–1067.

"9–(2–Deoxy–2–fluoro–β–D–arabinofuranosyl) guanine: A Metabolically Stable Cytotoxic Analogue of 2'–Deoxyguanosine", Montgomery et al., Journal of Medicinal Chemistry, 1986, 29, 2389.

"Synthesis and Biologic Activity of 2'–Fluoro–2–halo Derivatives of 9–β–D–Arabinofuranosyladenine[1]", Montgomery et al., Journal of Medicinal Chemistry 1992, 35.

"Liquid chromatographic study of acid stability of 2–chloro–2'–arabino–fluoro–2'–deoxyadenosine, 2–chloro–2'–deoxyadenosine and related analogs", Reichelova et al., J. Pharm. Biomed. Anal. (1995), 13 (4/5), 711–714.

"Synthesis and Anti–Hepatitis B Virus Activity of 9–(2–Deoxy–2–fluoro–β–L–arabinofuranosyl) purine Nucleosides", Ma et al., J. Med. Chem., 1997, 40, 2750–2754.

"Convergent Syntheses and Cytostatic Properties of 2–chloro–2'–deoxy–2'–fluoroadenosine and its N[7]–isomer", Bioorganic & Medicinal Chemistry Letters, Zaitseva, Galina V. et al, vol. 5, No. 24: 2999–3002, 1995, XP00223094: 3300.

Database CAPLUS on STN (Columbus, OH, USA), No. 122:260176 "Preparative high–performance liquid chromatographic separation of fluorodeoxy sugars", Evangelisto et al. Journal of Chromatography, 1995 695 (1), pp. 128–131.

* cited by examiner

METHOD FOR SYNTHESIZING 2-CHLORO-9-(2-FLUORO-β-D-ARABINOFURANOSYL)-9H-PURIN-6-AMINE

CROSS REFERENCE TO RELATED APPLICATIONS

This application claims the priority filing date of U.S. Provisional Patent Application No. 60/183,422 filed on Feb. 18, 2000.

STATEMENT REGARDING FEDERALLY SPONSORED RESEARCH OR DEVELOPMENT

This invention was made with support under U.S. Government Grant No. P01CA 34200 awarded by the National Cancer Institute. The U.S. Government has certain non-commercial rights in the invention.

FIELD OF THE INVENTION

This invention relates generally to methods for synthesizing a chemotherapeutic agent that is useful in the treatment of various malignancies. More particularly, this invention relates to improved methods for synthesizing 2-chloro-9-(2-deoxy-2-fluoro-β-D-arabinofuranosyl)-9H-p wherein the anionic form of a 2-chloro-6-substituted-purine is reacted with a protected and activated 2-deoxy-2-fluoro-D-arabinofuranose followed by reacting with an appropriate base such as ammonia to provide 2-chloro-9-(2-deoxy-2-fluoro-β-D-arabinofuranosyl)-9H-purin-6-amine. The present invention also relates to novel intermediates used in synthesizing the 2-chloro-9-(2-deoxy-2-fluoro-β-D-arabinofuranosyl)-9H-purin-6-amine such as 2-chloro-9-(2-deoxy-2-fluoro-β-D-arabinofuranosyl)-6-alkoxy-9H-purines and certain 2-chloro-6-substituted-9-(2-deoxy-2-fluoro-3,5-diprotected-β-D-arabinofuranosyl)-9H-purines.

BACKGROUND OF THE INVENTION

Clofarabine [2-chloro-9-(2-deoxy-2-fluoro-β-D-arabinofuranosyl)-9H-purin-6-amine] has exhibited cytotoxicity in mice inoculated with P388 leukemia. As reported by Montgomery et al., Synthesis and Biologic Activity of 2'-Fluoro-2-Halo Derivatives of 9-β-D-Arabinofuranosyladenine, *Journal of Medicinal Chemistry*, 1992, 35, pp. 397–401, clofarabine provided a good increase in life span of mice inoculated with P388 leukemia. The 2-chloro-9-(2-deoxy-2-fluoro-β-D-arabinofuranosyl)-9H-purin-6-amine was the most effective compound in the tested system. In addition, this compound exhibited reduced cleavage in vivo of the glycosidic bond as compared to Fludarabine.

The reported method for synthesizing 2-chloro-9-(2-deoxy-2-fluoro-β-D-arabinofuranosyl)-9H-purin-6-amine comprises a procedure using 3-O-acetyl-5-O-benzoyl-2-deoxy-2-fluoro-β-D-arabinofuranosyl bromide for the coupling with 2,6-dichloropurine, followed by an amination/deprotection sequence.(See Montgomery, et al., 9-(2-Deoxy-2-fluoro-β-D-arabinofuranosyl)guanine: A Metabolically Stable Cytotoxic Analogue of 2'-Deoxyguanosine, *Journal of Medicinal Chemistry*, 1986, 29, pp. 2389–2392; and Montgomery et al., Synthesis and Biologic Activity of 2'-Fluoro-2-halo Derivatives of 9-β-D-Arabinofuranosyladenine, *Journal of Medicinal Chemistry*, 1992, 35, pp. 397–401).

However, the reported method for synthesizing 2-chloro-9-(2-deoxy-2-fluoro-β-D-arabinofuranosyl)-9H-purin-6-amine in the range of about 13%. The described coupling reaction produced a mixture of nucleosides from which the desired 9-β intermediate was obtained in only 32% yield after careful chromatography. Direct amination/deprotection of this material gave the desired 2-chloro-9-(2-deoxy-2-fluoro-β-D-arabinofuranosyl)-9H-purin-6-amine, plus a partially benzoylated 2-chloro-9-(2-deoxy-2-fluoro-β-D-arabinofuranosyl)-9H-purin-6-amine that required further base treatment. Pure 2-chloro-9-(2-deoxy-2-fluoro-β-D-arabinofuranosyl)-9H-purin-6-amine was obtained only after several recrystallizations to remove salts and residual benzamide.

Such inefficient reactions will inhibit the ability to commercially produce 2-chloro-9-(2-deoxy-2-fluoro-β-D-arabinofuranosyl)-9H-purin-6-amine. Thus, there is a need for an improved method for synthesizing 2-chloro-9-(2-deoxy-2-fluoro-β-D-arabinofuranosyl)-9H-purin-6-amine that results in increased yields and/or reduced process steps.

SUMMARY OF THE INVENTION

One aspect of the present invention is to provide a relatively high-yield method of synthesizing 2-chloro-9-(2-deoxy-2-fluoro-β-D-arabinofuranosyl)-9H-purin-6-amine that comprises reacting the anionic form of a 2-chloro-6-substituted purine with a protected and activated 2-deoxy-2-fluoro-D-arabinofuranose to provide a 2,6-dichloro-9-substituted purine nucleoside. That product is then reacted with an alkoxide to provide a 2-chloro-6-alkoxy purine nucleoside. That compound is then reacted with ammonia to provide 2-chloro-9-(2-deoxy-2-fluoro-β-D-arabinofuranosyl)-9H-purin-6-amine.

Another aspect of the present invention relates to a method for synthesizing 2-chloro-9-(2-deoxy-2-fluoro-β-D-arabinofuranosyl)-9H-purin-6-amine by reacting the anionic form of a 2-chloro-6-substituted-purine with a protected and activated 2-fluoro-2deoxy-D-arabinofuranose to provide a reaction product comprising a purine nucleoside, followed by reacting the purine nucleoside with an appropriate base such as ammonia to provide 2-chloro-9-(2-deoxy-2-fluoro-β-D-arabinofuranosyl)-9H-purin-6-amine.

The present invention also relates to novel intermediates used in synthesizing the 2-chloro-9-(2-deoxy-2-fluoro-β-D-arabinofuranosyl)-9H-purin-6-amine. These intermediates include 2-chloro-9-(2-deoxy-2-fluoro-β-D-arabinofuranosyl)-6-alkoxy-9H-purines and 2-chloro-6-substituted-9-(2-deoxy-2-fluoro-3,5-diprotected-β-D-arabinofuranosyl)-9H-purines wherein the 6-substituent is selected from the group selected from amino, protected amino groups, azido and alkoxy.

Other features and objects and advantages of the present invention will become apparent from a reading of the following description.

BEST AND VARIOUS MODES FOR CARRYING OUT THE PRESENT INVENTION

Figure 1:
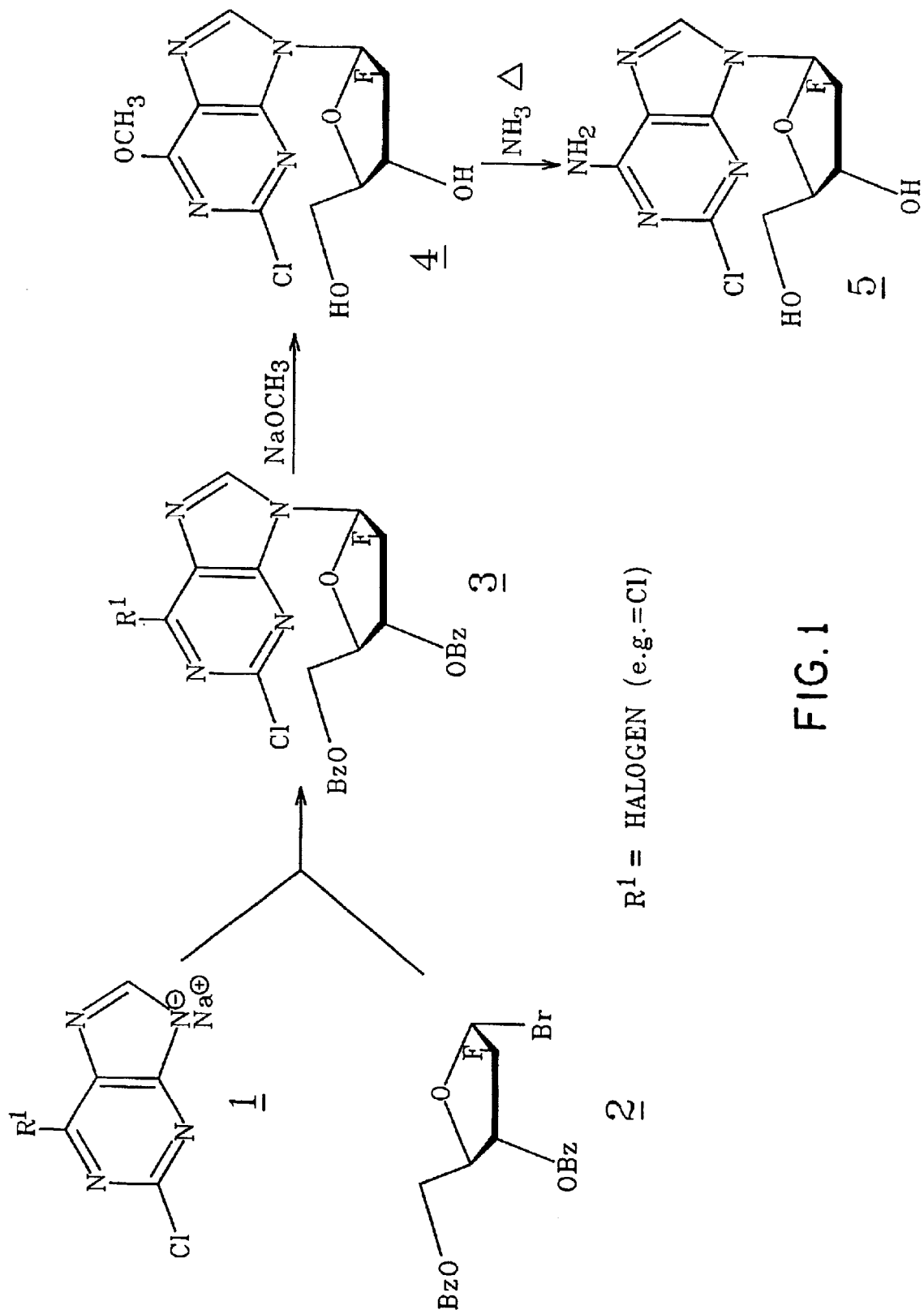
FIG. 1 is a schematic diagram of one embodiment of a reaction comprising a synthesis method of the present invention.

Reference to FIG. 1 illustrates one of the synthesis methods according to the present invention. This chemical reaction as illustrated in FIG. 1 provides a convenient process for preparing 2-chloro-9-(2-deoxy-2-fluoro-β-D-arabinofuranosyl)-9H-purin-6-amine(5) in three steps and has resulted in overall yields of about 44%.

For the first step, a protected and activated 2-deoxy-2-fluoro-D-arabinofuranose 2 is reacted with a 2-chloro-6-substituted purine 1 to provide a reaction product comprising a 9-substituted purine nucleoside 3. In this embodiment of the present invention, the preferred group in the 6 position is a halogen.

The preferred 2-chloro-6-substituted purine in the anionic form employed in this reaction scheme is 2,6-dichloropurine. Examples of suitable anionic forms include alkali metal salts, and organic amine salts. Alkali metal salts include sodium, potassium, and lithium salts. The metal salts can be obtained from metal hydrides such as NaH, KH and LiH or alkoxides such as $NaOCH_3$ and $KOCH_3$.

Organic bases for forming amine salts include hindered strong amine bases such as DBU(1,8-diazabicyclo [5.4.0] undec-7-ene); DBN (1,5-diazabicyclo [4.3.0]non-5-ene); Dabco (1,4-diazabicyclo [2.2.2] octane); and N,N-diisopropylethylamine.

A preferred anionic form is the sodium salt. The anionic form is needed to achieve the desired coupling reaction.

The 2-deoxy-2-fluoro-D-arabinofuranose contains protecting groups on the 3- and 5-hydroxyl groups and an activating group in the C-1 position.

Hydroxy protecting groups known in the art are described in Chapter 3 of the *Protective Groups in Organic Chemistry*, McOmie Ed., Plentum Press, New York (1973), and Chapter 2 of *Protective Groups in Organic Synthesis*, Greene, T., John Wiley and Sons, New York (1981and 1999); disclosures of which are incorporated herein by reference. Suitable protecting groups for the hydroxyl groups include ester forming groups, carbonates, alkyl ethers, aryl ethers, silyl ethers and carbonates. Examples of suitable esters are formyl, acetyl, substituted acetyl, propionyl, butynyl, pivaloyl, 2-chloroacetyl, benzoyl, substituted benzoyl, phenoxycarbonyl, methoxyacetyl and toluoyl.

Examples of carbonate derivates are phenoxycarbonyl, ethoxycarbonyl, butoxycarbonyl, vinyloxycarbonyl, 2,2,2-trichloroethoxycarbonyl and benzyloxycarbonyl.

Examples of alkyl ether and aryl ether forming groups are benzyl, p-chlorobenzyl, diphenylmethyl, triphenylmethyl, t-butyl, methoxymethyl, tetrahydropyranyl, allyl, tetrahydrothienyl, 2-methoxyethoxymethyl.

Examples of silyl ether forming groups are trialkysilyl, trimethylsilyl, isopropyldialkylsilyl, alkyldiisopropylsilyl, triisopropylsilyl, t-butyldialkylsilyl and 1,1,3,3-tetraisopropyldisiloxanyl.

Examples of carbamates are N-phenylcarbamate and N-imidazoylcarbamate.

Mixtures of protecting groups can be employed if desired. For example, the 2-deoxy-2-fluoro-D-arabinofuranose 2 may have either two acyl groups, two ether groups, or combinations of acyl and ether groups.

Examples of activating groups for the C-1 of the carbohydrate include halogen such as Cl, Br and F; alkylsulfonyloxy, substituted alkylsulfonyloxy; arylsulfonyloxy, and substituted arylsulfonyloxy.

Suitable alkyl substituents contain 1–8 carbon atoms and mole typically 1–4 carbon atoms such as methyl, ethyl and propyl. A suitable aryl group includes phenyl.

Examples of alkyl- and substituted alkyl-sulfonyloxy groups are methanesulfonyloxy and 2-chloroethanesulfonyloxy.

Examples of aryl- and substituted aryl-sulfonyloxy groups are benzenesulfonyloxy, toluenesulfonyloxy, p-nitrobenzenesulfonyloxy and p-bromobenzenesulfonyloxy; while most preferred is methanesulfonyloxy.

A preferred protecting group is benzoyl and a preferred activating group is bromine. A specific compound that may be used as sugar compound 2 is 2-deoxy-2-fluoro-3,5-di-O-benzoyl-α-D-arabinofuranosyl bromide as prepared by C. H. Tann, et al., *J. Org. Chem.*, 1985, 50, 3644–3647; the disclosure of which is hereby incorporated by reference.

The purine and activated carbohydrate derivative are typically employed in approximately equivalent amounts or with an excess of the purine and more typically about 1:1 to about 3:1; preferably about 1:1 to about 1.5:1 and more preferably about 1:1 to about 1.2:1 of purine to activated carbohydrate derivative.

This step of the process is typically carried out at temperatures of about 0° to about 100° C., more typically about 20° C. to about 70° C. and preferably about 20° C. to about 40° C.; and at normal atmospheric pressures. However, higher or lower pressures can be employed if desired. This step of the process typically takes about 3 to about 24 hours for completion.

The reaction of the above-described purine compound 1 with the arabinofuranose sugar 2 preferably takes place in the presence of a solvent. Such solvent may be a dipolar, aprotic solvent such as acetone, acetonitrile, dimethylformamide, dimethyl sulfoxide, sulfolane, dimethylacetamide and ethers such as tetrahydrofuran, dioxane, and dimethoxyethane.

When the reaction of the purine 1 and arabinofuranose sugar 2 is complete, the reaction mixture may be filtered and the solvent may be evaporated until a foam is obtained. The foam may be purified on flash silica using isopropyl acetate/hexane or any other suitable solution as the eluent. The fractions containing the desired 9-β isomer may be combined and evaporated to a residue that may then be crystallized from ethanol to give the desired 9-substituted purine nucleoside 3.

For the next step, the 9-substituted purine-nucleoside 3 is reacted with an alkoxide to provide the corresponding 2-chloro-6-alkoxy purine nucleoside 4. The alkoxide is preferably an alkali metal alkoxide and most preferably sodium methoxide.

This step of the process is typically carried out at temperatures of about 0° C. to about 100° C., more typically about 20° C. to about 40° C., and at normal atmospheric pressures. Higher or lower pressures can be employed, if desired. This step of the process typically takes about 3 to about 24 hours for completion.

Moreover, this step of the process preferably takes place in the presence of a solvent, with a preferred solvent being an alcohol which corresponds to the alkoxide used in the reaction. Upon completion, the reaction mixture may be treated with an ion exchange resin, filtered and evaporated to a residue. One commercially available ion exchange resin that has proved useful for this purpose is Dowex 50WX8–400 ion-exchange resin.

The desired 6-alkoxypurine nucleoside 4 may be derived from the residue obtained in this step by triturating the residue with hexane several times, followed by decantation of the supernatant liquor. The residue thus obtained may then be either recrystallized, or slurried in cold isopropyl alcohol in lieu of recrystallization, to give 6-alkoxypurine nucleoside 4.

Finally, 2-chloro-9-(2-deoxy-2-fluoro-β-D-arabinofuranosyl)-9H-purin-6-amine (5) may be obtained by reacting the 6-alkoxypurine nucleoside 4 and ammonia.

This step of the process is typically carried out at temperatures of about 20° C. to about 120° C. and more typically about 70° C. to about 100° C.; and typically at pressures generated in a sealed vessel at the above temperatures. This step of the process typically takes about 12 hours to about 24 hours for completion.

This step of the process can be carried out in the presence of an alcoholic solvent such as methanol or ethanol or in the absence of a solvent.

The ammonia is typically present as an alcoholic solution such as in methanol or ethanol (typically saturated at 5° C.). In a preferred embodiment, this reaction takes place in a stainless steel bomb at 80° C. (65 psi). When the reaction is completed, the solvent may be removed and the residue dissolved in refluxing methanol, and preferably hot-filtered. Upon cooling, the crude product 2-chloro-9-(2-deoxy-2-fluoro-β-D-arabinofuranosyl)-9H-purin-6-amine (5) may be isolated by filtration. The product may be recrystallized from methanol to give high-quality -2-chloro-9-(2-deoxy-2-fluoro-β-D-arabinofuranosyl)-9H-purin-6-amine (5). Further recrystallizations of evaporated filtrates from methanol are optional to obtain additional 2-chloro-9-(2-deoxy-2-fluoro-β-D-arabinofuranosyl)-9H-purin-6-amine (5).

Figure 2:
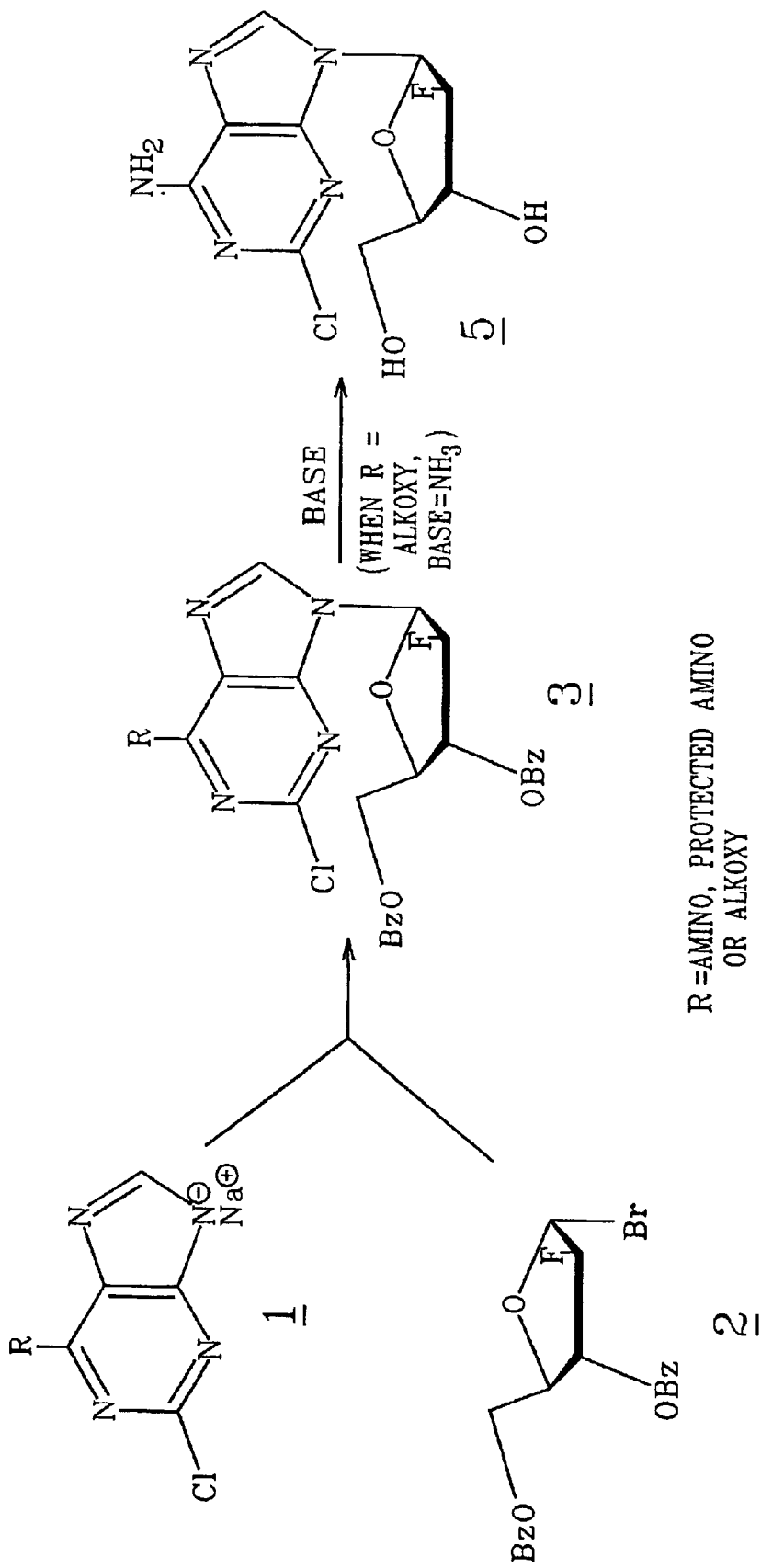
FIG. 2 is a schematic diagram of an alternative embodiment of another synthesis method according to the present invention.

Reference to FIG. 2 illustrates another reaction scheme according to the present invention for synthesizing 2-chloro-9-(2-deoxy-2-fluoro-β-D-arabinofuranosyl)-9H-purin-6-amine (5).

In the first step, a protected and activated 2-deoxy-2-fluoro-D-arabinofuranose 2 is reacted with the anionic form of a 2-chloro-6-substituted purine 1 to provide a reaction product comprising a 9-substituted purine nucleoside 3. Examples of suitable substituents in the 6 position include groups such as amino, protected amino groups, azido and alkoxy, with amino being preferred. Suitable alkoxy groups are methoxy and ethoxy.

Suitable amino protecting groups are acyl, imino, and carbamates. Suitable acyl groups are acetyl-, benzoyl-, p-methoxybenzoyl, 2-methylbutryl- and pivaloyl.

A suitable imino group is dimethylaminomethylene.

Suitable carbamates are isobutyl-, t-butyl-, benzyl-, p-methoxybenzyl-, carbamates.

The preferred purine is the anionic form of 2-chloro-6-aminopurine. Examples of suitable anionic forms include alkali metal salts and organic amine salts as discussed above in the first embodiment of the present invention. Preferred anionic forms are the sodium salt and amine salts such as DBU.

The 2-deoxy-2-fluoro-D-arabinofuranosyl moiety contains protecting groups on the 3- and 5-hydroxyl groups and an activating group in the C-1 position.

Examples of suitable protecting groups and activating groups are those discussed above for the first embodiment according to the present invention.

A preferred protecting group is benzoyl and a preferred activating group is bromine.

A specific compound that may be used as the sugar reactant 2 is 2-deoxy-2-fluoro-3,5-di-O-benzoyl-2-α-D-arabinofuranosyl bromide.

The purine and the activated carbohydrate derivative are typically employed in approximately equivalent amounts or with an excess of the purine and more typically about 1:1 to about 3:1, preferably about 1:1 to about 1.5:1 and more preferably about 1:1 to about 1.2:1 of purine to the activated carbohydrate derivative.

This step of the process is typically carried out at temperatures of about 0° C. to about 100° C., more typically about 20° C. to about 70° C. and preferably about 20° C. to about 40° C.; and at normal atmospheric pressures. However, higher or lower pressures can be employed if desired. This step of the process typically takes about 3 to about 96 hours for completion.

The reaction of the above-described purine compound 1 with the arabinofuranose sugar 2 preferably takes place in the presence of a solvent. Such solvent may be a dipolar, aprotic solvent such as acetone, acetonitrile, dimethylformamide, dimethyl sulfoxide, sulfolane, dimethylacetamide, and ethers such as tetrahydrofuran, dioxane and dimethoxyethane.

Upon completion of the reaction of the purine 1 and arabinofuranose sugar 2, the reaction mixture may be filtered and the solvent may be evaporated until a foam is obtained. The foam may be purified on flash silica using isopropyl acetate/hexane or any other suitable solution of the eluent. The fractions containing the desired 9-β isomer may be combined and evaporated to a residue that may then be recrystallized from ethanol to give the desired 9-substituted purine nucleoside 3.

When the group in the 6 position is amino or a protected amino group, the desired 2-chloro-9-(2-deoxy-2-fluoro-β-D-arabinofuranosyl)-9H-purin-6-amine (5) may be obtained by reacting the purine nucleoside 3 and a base such as ammonia and/or an alkali metal alkoxide such as sodium methoxide, an alkali metal carbonate such as sodium carbonate, and a alkali metal hydroxide such as lithium hydroxide. This step of the process with these groups is typically carried out at temperatures of about −20° C. to about 80° C. and more typically about 0° C. to about 50° C.; and typically at pressures generated in a sealed vessel at the above temperatures. This step of the process typically takes about 1 hour to about 24 hours for completion.

Figure 3:
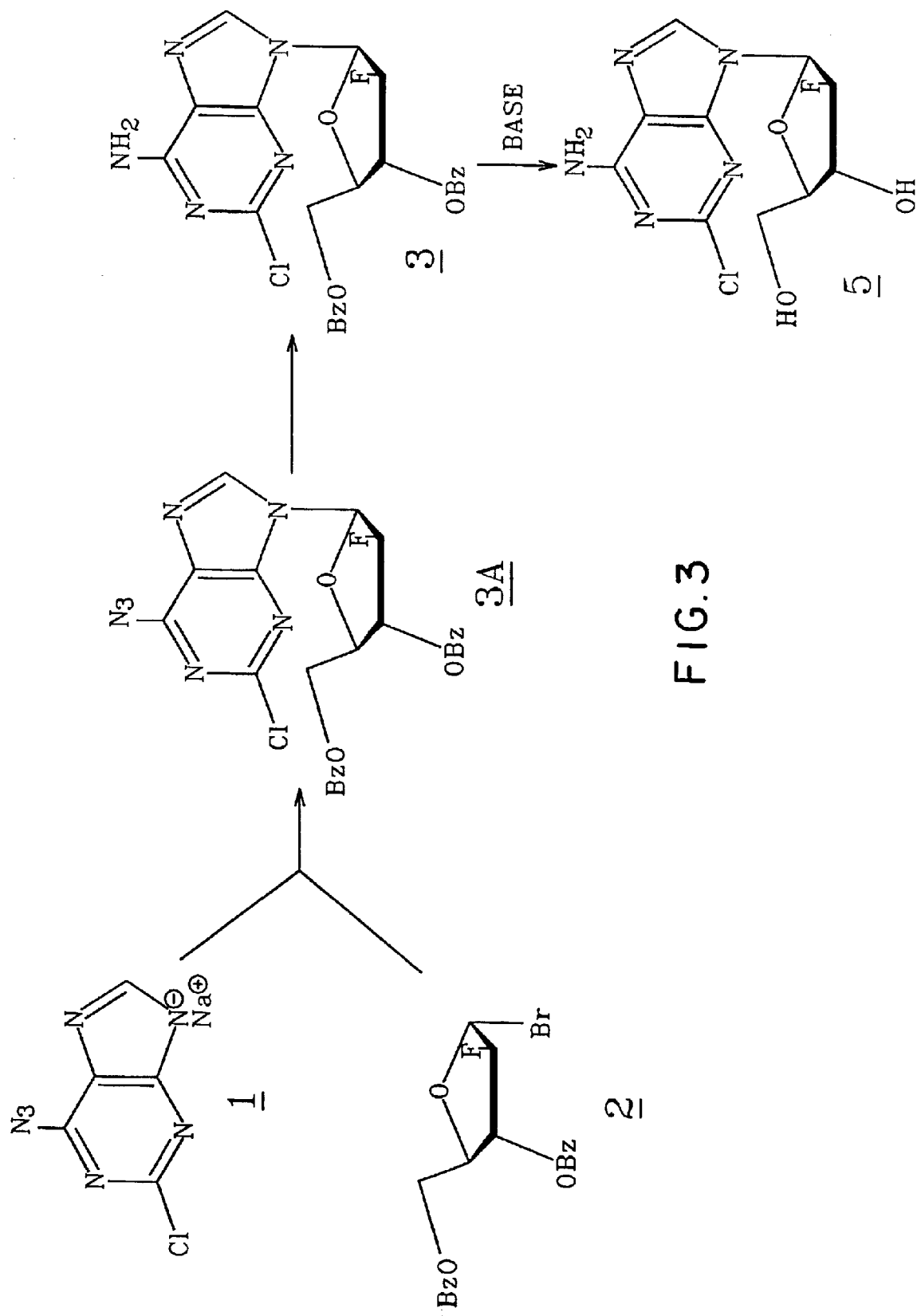
FIG. 3 is a schematic diagram of an alternative embodiment of a further synthesis method according to the present invention.

When the group in the 6 position is azido, the desired 2-chloro-9-(2-deoxy-2-fluoro-β-D-arabinofuranosyl)-9H-purin-6-amine(5) may be obtained by reacting the purine nucleoside 3A with a reducing agent such as a hydrogenating agent to reduce the azido group to an amino group and then reacting with a base as discussed above(see FIG. 3). The reducing step can be carried out, for instance, by reacting with hydrogen in the presence of a hydrogenation catalyst such as platinum or palladium. This step of the process is typically carried out at about normal room temperatures and a pressure of about 1 atm to about 3 atm. Moreover, when the group in the 6 position is azido, the order of the reaction steps can be reversed. In particular, the desired 2-chloro-9-(2-deoxy-2-fluoro-β-D-arabinofuranosyl)-9H-purin-6-amine (5) may also be obtained by reacting the purine nucleoside 3 with a base as discussed above and then reacting with a reducing agent to reduce the azido group to an amino group.

When the group in the 6 position is alkoxy, the desired 2-chloro-9-(2-deoxy-2-fluoro-β-D-arabinofuranosyl)-9H-purin-6-amine (5) may be obtained by reacting the purine nucleoside 3 with ammonia.

This step of the process is typically carried out at about normal room temperatures to about 120° C. and more typically about 70° C. to about 100° C.; and typically at pressures generated in a sealed vessel at the above temperatures. This step of the process typically takes about 12 hours to about 24 hours for completion.

This step of the process is preferably carried out in the presence of an alcoholic solvent, such as methanol or ethanol or in the absence of a solvent.

Preferred embodiments for converting 3 to 5 include using ammonia or sodium methoxide. In the examples where the group (R in 3 in FIG. 2) is amino, protected amino such as acylamino, imino, and carbamate, one preferred embodiment is to use sodium methoxide at about 0° C. to normal room temperatures. Alternatively, ammonia can be used.

The ammonia, when used, is typically present as an alcoholic solution such as in methanol or ethanol (typically saturated at 5° C.). In a preferred embodiment, this reaction takes place in a stainless steel bomb at room temperature. When the reaction is completed, the solvent may be removed and the residue dissolved in refluxing methanol, and preferably hot-filtered. Upon cooling, the crude product 2-chloro-9-(2-deoxy-2-fluoro-β-D-arabinofuranosyl)-9H-purin-6-amine (5) may be isolated by filtration. The product may be recrystallized from methanol to give high-quality 2-chloro-9-(2-deoxy-2-fluoro-β-D-arabinofuranosyl)-9H-purin-6-amine (5). Further recrystallizations of the evaporated filtrates from methanol are optional to obtain additional 2-chloro-9-(2-deoxy-2-fluoro-β-D-arabinofuranosyl)-9H-purin-6-amine (5).

One of ordinary skill in the art will readily see that some modification may be made to the preferred embodiments of the present invention set forth above. Further illustration of the present invention is set forth in the following examples, which are not to be construed as limiting the invention in any manner. The examples illustrate the individual steps of the above-described invention process.

EXAMPLE 1

2,6-Dichloro-9-(2-deoxy-2-fluoro-3,5-di-β-benzoyl-β-D-arabinofuranosyl)-9H-purine(3) (FIG. 1. $R^1=$ Cl)

A suspension of 2,6-dichloropurine (4.0 g, 21.2 mmol) in anhydrous acetonitrile (130 ml) at room temperature was treated with NaH (916 mg of 60% in oil washed with heptane, 22.9 mmol), and the mixture was stirred 15 minutes under argon. To this stirred suspension, a solution of 2-deoxy-2-fluoro-3,5-di-O-benzoyl-α-D-arabinofuranosyl bromide (C. H. Tann, et al., *J. Org Chem.*, 1985, 50, 3644–3647; 9 g, 21.3 mmol) in acetonitrile (29 ml) was added dropwise, and the mixture was stirred at room temperature overnight. Insoluble material was removed by filtration and washed with acetonitrile and chloroform. The combined filtrate and washings were evaporated to a near glass. A chloroform solution of this residue was applied to a flash column containing silica gel 60 (70–230 mesh, E. Merck). Elution with chloroform provided pure fractions that were combined and crystallized from boiling ethanol to give 1.6 g (14%) pure product (HPLC, 100% 9-β). Material from less pure fractions was crystallized from chloroform at 5° C., 6.3 g(56%) (HPLC, 97% 9-β, 3% 9-α). After structure confirmation by 'H NMR, this material was used directly in the next step.

EXAMPLE 2

2-Chloro-9-(2-deoxy-2-fluoro-β-D-arabinofuranosyl)-6-methoxy-9H-purine(4)

2,6-Dichloro-9-(2-deoxy-2-fluoro-3,5-di-O-benzoyl-β-D-arabinofuranosyl)-9H-purine(3) (4.7g, 8.85 mmol) prepared as in Example 1 was suspended in anhydrous methanol (200 ml) at room temperature. To this mixture, a 25 wt % solution of sodium methoxide in methanol (2.23 ml, 9.75 mmol) was added in one portion. After being stirred for 1.5 hours, the reaction became a clear solution. After 20 hours, the reaction was neutralized with a strong cation exchange resin (Dowex 50x4[$H^{30}$]) which was collected after 15 minutes and washed with methanol. The combined filtrate was subjected to evaporation and was led to provide a gum that was triturated with two portions of petroleum ether 30–60° C. (decanted). The remaining material was dissolved in hot 2-propanol (30 ml)(filtered to clarity), and the solution was allowed to deposit crystals at room temperature before being chilled (5° C.) overnight. The product was collected, washed with ice-cold 2-propanol, and dried in vacuo to give the title compound, 1.7 g (60%), mp 199–200° C. (HPLC, 98%). Flash chromatography of the evaporated filtrate (silica gel 60, 70–230 mesh, E. Merck) with 95.5 chloroform-methanol as solvent provided additional material, 0.55 g(20%), mp 196–197° C. (HPLC, 96%).

EXAMPLE 3

2-Chloro-9-(2-deoxy-2-fluoro-β-D-arabinofuranosyl)-9H-purin-6-amine(5)

2-Chloro-9-(2-deoxy-2-fluoro-β-D-arabinofuranosyl)-6-methoxy-9H-purine(4) (6.2 g, 19.5 mmol) prepared as in Example 2 was placed in a stainless steel pressure bomb with 300 ml ethanol saturated (0° C.) with anhydrous ammonia. The sealed vessel was heated at 80° C. for 16 hours. More ethanolic ammonia (30 ml) was added to the incomplete reaction, and heating was continued for 4 hours. The reaction solution containing a trace of starting material was evaporated to a white foam that crystallized from hot methanol (75 ml), 5.1 g. This relatively pure material was dissolved in refluxing methanol (110 ml), filtered, allowed to cool to room temperature, then chilled. Pure title compound was obtained in two crops, total 4.6 g (78%), mp 231° C. (HPLC, 99%).

EXAMPLE 4

2-Chloro-9-(2-deoxy-2-fluoro-3,5-di-O-benzoyl-β-D-arabinofuranosyl)-9H-purin-6-amine(3) (FIG. 2, R=amino)

A suspension of 2-chloroadenine (21 mg, 0.12 mmol) in anhydrous acetonitrile (2.5 ml) at room temperature was treated dropwise with 98% DBU (18 μl, 0.12 mmol), and the mixture was stirred 25 minutes under argon. To this stirred suspension, a solution of 2-deoxy-2-fluoro-3,5-di-O-benzoyl-α-D-arabinofuranosyl bromide (2) (48 mg, 0.1 mmol) in acetonitrile (0.8 ml) was added dropwise. The mixture was stirred at room temperature until the 2-deoxy-2-fluoro-3,5-di-O-benzoyl-α-D-arabinofuranosyl bromide (2) was consumed. After 96 hours, insoluble material was removed by filtration and washed with $CHCl_3$. The combined filtrates were evaporated to a residue that was dissolved in $CHCl_3$. This solution was applied to a preparative layer silica gel plate (Analtech, 10x20 cm, 1,000 microns) that was developed twice in 97:3 $CHCl_3$/MeOH. Product bands were extracted with 1:1 $CHCl_3$/MeOH, and the extracts were evaporated to give white solids, 16 mg (28%) (HPLC, 100% 9-β) and 20 mg (34%) (HPLC, 97% 9-α).

The above description and examples of the present invention are not intended to be limiting, and it is recognized that one of skill in the art will readily discern variations of this description, that are intended to be included within the spirit and scope of the invention.

What is claimed is:

1. A method for synthesizing 2-chloro-9-(2-deoxy-2-fluoro-β-D-arabinofuranosyl)-9H-purin-6-amine which comprises:
   a) reacting the anionic form of a 2-chloro-6-substituted purine with a protected and activated 2-deoxy-2-fluoro-D-arabinofuranose; wherein the purine is substituted at position 6 with a member selected from the group consisting of halogen, amino, and protected amino;
   b) reacting the product from a) with an alkoxide to provide 2-chloro-6-alkoxy purine nucleoside; and
   c) reacting the 2-chloro-6-alkoxy purine nucleoside with ammonia to provide the 2-chloro-9-(2-deoxy-2-fluoro-β-D-arabinofuranosyl)-9H-purin-6-amine.

2. The method of claim 1 wherein the 6-substituted group in the 2-chloro-6-substituted-purine is a halogen.

3. The method of claim 1 wherein the 6-substituted group in the 2-chloro-6-substituted-purine is chlorine.

4. The method of claim 1 wherein the anionic form is an alkali metal salt or organic amine salt.

5. The method of claim 1 wherein the anionic form is an alkali metal salt.

6. The method of claim 5, wherein the alkali metal is sodium.

7. The method of claim 1 wherein the protecting group on the 3- and 5-hydroxyls of the 2-deoxy-2-fluoro-D-arabinofuranose is selected from the group consisting of an acyl group, ether group, and combinations thereof, and wherein the activating group at C-1 of the 2-deoxy-2-fluoro-D-arabinofuranose is selected from the group consisting of halo, alkylsulfonyloxy, and arylsulfonyl groups.

8. The method of claim 1 wherein the 2-deoxy-2-fluoro-D-arabinofuranose is 2-deoxy-2-fluoro-3,5-di-O-benzoyl-α-D-arabinofuranosyl bromide.

9. The method of claim 1 wherein the reaction of 2-chloro-6-substituted purine with the 2-deoxy-2-fluoro-D-arabinofuranose takes place in the presence of a dipolar, aprotic solvent.

10. The method of claim 9 wherein the solvent is selected from the group consisting of acetone, acetonitrile, dimethylformamide, dimethyl sulfoxide, sulfolane, dimethylacetamide, and an ether.

11. The method of claim 1 wherein the alkoxide is an alkaline metal alkoxide.

12. The method of claim 11 wherein the alkoxide is methoxide.

13. The method of claim 1 wherein the alkoxide is sodium methoxide.

14. The method of claim 1 wherein the reaction of step (b) takes place in the presence of a solvent.

15. The method of claim 14 wherein the solvent is an alcohol corresponding to the alkoxide of step (b).

16. The method of claim 1 wherein step (c) takes place in the presence of a solvent.

17. The method of claim 16 wherein the solvent is an alcohol.

18. The method of claim 1 wherein the ammonia is present as an alcoholic solution.

19. The method of claim 18 wherein the alcoholic solution is in methanol or ethanol.

20. A method for synthesizing 2-chloro-9-(2-deoxy-2-fluoro-βD-arabinofuranosyl)-9H-purin-6-amine which comprises:
   a) reacting the anionic form of a 2-chloro-6-substituted purine with a protected and activated 2-deoxy-2-fluoro-D-arabinofuranose; wherein the 6-substituted group in the 2-chloro-6-substituted purine is alkoxy; and then
   (b) reacting with ammonia to provide the 2-chloro-9-(2-deoxy-2-fluoro-β-D-arabinofuranosyl)-9H-purin-6-amine.

21. The method of claim 20 wherein the alkoxy is methoxy or ethoxy.

22. The method of claim 20 wherein the anionic form is en alkali metal salt or organic amine salt.

23. The method of claim 20 wherein the anionic form is an alkali metal salt.

24. The method of claim 23, wherein the alkali metal is sodium.

25. The method of claim 20 wherein the anionic form is an organic amine salt.

26. The method of claim 25, wherein the organic amine salt is DBU.

27. The method of claim 20 wherein the protecting group on the 3- and 5-hydroxyls of the 2-deoxy-2-fluro-D-arabinofuranose is selected from the group consisting of an acyl group, ether group, and combinations thereof, and wherein the activating group at C-1 of the 2-deoxy-2-fluoro-D-arabinofuranose is selected from the group consisting of halo, alkylsulfonyloxy, and arylsulfonyl groups.

28. The method of claim 20 wherein the 2-deoxy-2-fluoro-D-arabinofuranose is 2-deoxy-2-fluoro-3,5-di-O-benzoyl-β-D-arabinofuranose bromide.

29. The method of claim 20 wherein the reaction of the 2-chloro-6-substituted purine with the 2-deoxy-2-fluoro-D-arabinofuranose takes place in the presence of a dipolar, aprotic solvent.

30. The method of claim 29 wherein the solvent is selected from the group consisting of acetone, acetonitrile, dimethylformamide, dimethyl sulfoxide, sulfolane, dimethylacetamide, and an ether.

31. The method of claim 20 wherein step (b) takes place in the presence of a solvent.

32. The method of claim 31 wherein the solvent is an alcohol.

33. The method of claim 20 wherein the ammonia is present as an alcoholic solution.

34. The method of claim 33 wherein the alcoholic solution is in methanol or ethanol.

* * * * *

UNITED STATES PATENT AND TRADEMARK OFFICE
CERTIFICATE OF CORRECTION

PATENT NO. : 6,949,640 B2
DATED : September 27, 2005
INVENTOR(S) : John A. Montgomery et al.

It is certified that error appears in the above-identified patent and that said Letters Patent is hereby corrected as shown below:

<u>Title page,</u>
Item [54], Title, should read as follows:
-- METHODS FOR SYNTHESIZING 2-CHLORO-9-(2-DEOXY-2-FLUORO-β-D-ARABINOFURANOSYL)-9H-PURIN-6-AMINE --.

Signed and Sealed this

Twenty-ninth Day of November, 2005

JON W. DUDAS
*Director of the United States Patent and Trademark Office*